(12) United States Patent
Wu et al.

(10) Patent No.: US 10,667,780 B2
(45) Date of Patent: Jun. 2, 2020

(54) CONTRAST CARRIER DEVICE WITH GEOMETRIC CALIBRATION PHANTOM ON COMPUTED TOMOGRAPHY

(71) Applicant: National Yang-Ming University, Taipei (TW)

(72) Inventors: Meng-Tse Wu, Taipei (TW);
Shih-Chun Jin, Taipei (TW);
Jyh-Cheng Chen, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 16/267,905

(22) Filed: Feb. 5, 2019

(65) Prior Publication Data

US 2020/0015771 A1  Jan. 16, 2020

(30) Foreign Application Priority Data

Jul. 10, 2018 (TW) .............................. 107123887 A (51) Int. Cl.
*A61B 6/00* (2006.01)
*G06T 11/00* (2006.01)
*A61B 6/03* (2006.01)
*G01T 7/00* (2006.01)

(52) U.S. Cl.
CPC .............. *A61B 6/583* (2013.01); *A61B 6/032* (2013.01); *G01T 7/005* (2013.01); *G06T 11/005* (2013.01)

(58) Field of Classification Search
None
See application file for complete search history.

(56) References Cited

U.S. PATENT DOCUMENTS

| 8,966,954 B2 * | 3/2015 | Ni ........................ G09B 23/286 73/1.86 |
| 2004/0005035 A1 * | 1/2004 | White .................... A61B 6/583 378/207 |
| 2005/0008126 A1 * | 1/2005 | Juh ......................... A61B 6/12 378/207 |

* cited by examiner

*Primary Examiner* — Hoon K Song
(74) *Attorney, Agent, or Firm* — Muncy, Geissler, Olds & Lowe, P.C.

(57) ABSTRACT

The invention provides a contrast carrier device with geometric calibration phantom on computed tomography, comprising: a front ring body having a front outer peripheral surface; the front outer peripheral surface is provided with a front correction bead; a loading table, wherein one end of the loading table is connected with the front ring body; a rear ring body is oppositely arranged at the other end of the front ring body connected to the loading table, wherein the rear ring body has an outer peripheral surface, the rear peripheral surface is provided with a rear correction bead; a virtual axis passes through the center of the front ring body and the center of the rear ring body, respectively, and the front correction bead and the rear correction bead. The beads are arranged equidistantly along the virtual axis; and a support body is provided opposite to the other end of the rear ring body connected to the loading table, so that the contrast carrier device is fixed to a tomography scan, and the virtual axis coincide with a scan axis of the tomography device.

14 Claims, 14 Drawing Sheets

CONTRAST CARRIER DEVICE WITH GEOMETRIC CALIBRATION PHANTOM ON COMPUTED TOMOGRAPHY

CROSS-REFERENCE TO RELATED APPLICATIONS

This Non-provisional application claims priority under 35 U.S.C. § 119 on Patent Application No(s). TW107123887 filed in Taiwan, Republic of China, Jul. 10, 2018, the entire contents of which are hereby incorporated by reference.

BACKGROUND OF INVENTION

Field of the Invention

The present invention provides a geometric calibration phantom, especially about a tomography phantom combined with loading table, the image correction and image photography can be performed simultaneously through one step, there are precision tomography and time saving effects.

Description of Related Art

The computed tomography (CT) is now used in many fields. In medicine, the CT assists doctors in diagnosing the patients, the three-dimensional body images of the patients are obtained from CT, there are better effects on preoperative treatment plan or diagnosing lesion. The industrial CT plays a very important role in industrial inspection, the objects' defects can be detected more effectively and rapidly when inspecting integrated circuit packages, disregarding the dose, and the resolution is very high.

Furthermore, the micro-computed tomography (micro-CT) is now used in different studies extensively. It can be used in the non-invasive experiment on experimental rats or insects, the internal information of living animals can be obtained faster, and the quantity of living animals sacrificed can be reduced. In addition, the micro-CT plays a very important role in in-vitro dental application, helping the dentists diagnose the patients' teeth.

The image reconstruction is always an important research field of CT, the images at different angles are collected, and then the stereo image in the space is calculated and reconstructed. In reconstruction, the geometric architecture of mechanism will influence the reconstructed image quality severely. Ideally, the focal spot of X-ray tube of the overall mechanism and the center of detector are on the same straight line, and the overall mechanism revolves round the rotation center of the irradiated object, and the rotation center is perpendicular to the straight line. However, in practical situation, due to human error or gravity problem, the mechanism revolution causes larger geometric errors over time. Therefore, the geometric correction is required before CT acquisition or reconstruction, so as to obtain the projection image approximating to practical situation. The purpose of geometric correction is find out geometrical deviation by using some image analysis techniques, the geometric parameters of deviation are found out and substituted in the re-mapping step, the original projection image with deviation is corrected, and substituted in image reconstruction at last.

The geometric correction is always a very important part of the research on stereo image reconstruction. The present invention develops a self-made contrast carrier device for geometric correction, particularly, the cone-beam CT (CBCT) is used in many fields to obtain the profile images of objects. There are two main methods for geometric correction. One method uses the projection image of specific phantom to analytically work out geometric parameters. The drawback in this method is that the geometric parameters shall be worked out before experiment, but the gantry may have geometry changes between two scans. The other method is synchronous geometric correction. The user can figure out geometric parameters by scanning the object once. The disadvantage in this method is that it cannot calculate all complete geometric parameters. This contrast carrier device can overcome the aforesaid problems effectively, further enhancing the reconstructed image quality.

BRIEF SUMMARY OF THE INVENTION

A specific phantom shall be used before the existing tomography is used, so as to check whether the plane where the object is located deviates from the scan axis or not. If yes, the subsequent 3D image construction may have deviation or distortion, even if the correction is completed or in long-term operation, the corrected plane may deviate because of human factors or mechanical actions. These uncertainties influence the use of the existing tomography device greatly.

In view of this, the present invention combines loading table and phantom into "two-in-one" form, the tomography performing image correction and image photography simultaneously through one step is implemented, which has precision tomography and time saving effects.

The contrast carrier device with geometric calibration phantom on computed tomography provided by the present invention comprises a front ring body with a front outer peripheral surface, the front outer peripheral surface is provided with a front correction bead; a loading table, wherein one end of the loading table is connected with the front ring body; a rear ring body, the rear ring body is oppositely arranged at the other end of the front ring body connected to the loading table, wherein the rear ring body has a rear outer peripheral surface, the rear outer peripheral surface is provided with a rear correction bead; a virtual axis passes through the center of the front ring body and the center of the rear ring body respectively, the front correction bead and the rear correction bead are arranged equidistantly along the virtual axis; and a support body, the support body is provided opposite to the other end of the rear ring body connected to the loading table, so that the contrast carrier device is fixed to a tomography device, and the virtual axis coincides with a scan axis of the tomography device.

The present invention provides a correction method for tomography instruments, the steps include (a) the aforesaid contrast carrier device is fixed in the middle of a tomography device, and the contrast carrier device has a virtual axis which coincides with a scan axis of the tomography device; (b) a 2D projection (Object images) image and a reference image normal to the straight line from a light source point to the scan axis are obtained by using the tomography instrument based on the scan axis, wherein the reference image has at least two reference points (Dual ring images); (c) the at least two reference points are substituted in an algorithm, at least two geometric parameter points are obtained; (d) an ideal plane is established by using the at least two geometric parameter points and the scan axis, the 2D projection image (Object images) is reprojected on the ideal plane; and (e) a 2D reconstruction image is obtained from the ideal plane.

In order to attain the aforesaid and other purposes, one or more specific embodiments of the present invention are described below. The other features or advantages of the present invention are elaborated in embodiments and claims.

DETAILED DESCRIPTION OF THE INVENTION

Figure 1:
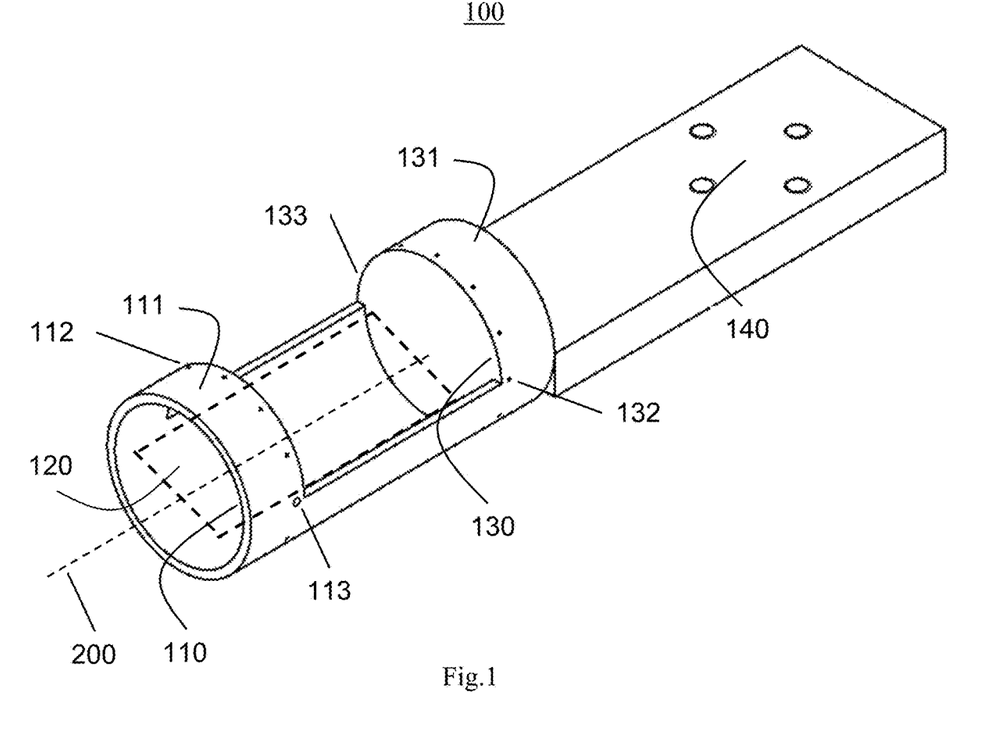
FIG. 1 is the structural representation of the contrast carrier device of the present invention.

The contrast carrier device with geometric calibration phantom on computed tomography 100 provided by the present invention, according to FIG. 1, comprising a front ring body 110 with a front outer peripheral surface 111, the front outer peripheral surface 111 is provided with a front correction bead 112; a loading table 120, wherein one end of the loading table 120 is connected with the front ring body 110; a rear ring body 130, the rear ring 130 is oppositely arranged at the other end of the front ring body 110 connected to the loading table 120, wherein the rear ring body 130 has a rear outer peripheral surface 131, the rear outer peripheral surface 131 is provided with a rear correction bead 132; a virtual axis 200 passes through the center of the front ring body 110 and the center of the rear ring body 130 respectively, the front correction bead 112 and the rear correction bead 132 are arranged equidistantly along the virtual axis 200; and a support body 140, the support body is provided opposite to the other end of the rear ring body 130 connected to the loading table 120, so that the contrast carrier device 100 is fixed to a tomography device, and the virtual axis 200 coincides with a scan axis of the tomography device.

Preferably, the front outer peripheral surface 111 is provided with a plurality of front positioning beads 113, wherein the plurality of front positioning beads 113 and the front correction bead 112 are equiangularly arranged on the front outer peripheral surface 111 by the virtual axis 200. The rear outer peripheral surface 131 is provided with a plurality of rear positioning beads 133, wherein the plurality of rear positioning beads 133 and the rear correction bead 131 are equiangular arranged on the rear outer peripheral surface 131 by the virtual axis 200, and the plurality of front positioning beads 113 and the plurality of rear positioning beads 133 are arranged equidistantly along the virtual axis 200 pairwise.

Preferably, the front correction bead 112, the rear correction bead 131, the plurality of front positioning beads 113 and the plurality of rear positioning beads 133 are made of a high density material. In an embodiment, the high density material can be metal or a material which can be imaged in X-ray image in relation to others, and the material provides over 10 times of contrast, so that it presents approximately complete attenuation in X-ray image.

Preferably, the diameter ratio range of the front correction bead 112, the rear correction bead 131, the plurality of front positioning beads 113 and the plurality of rear positioning beads 133 is 1:1:0.1~0.4:0.1~0.4. In an embodiment, the ratio range is 1:1:0.22~0.32:0.22~0.32.

Preferably, the front ring body 110, the loading table 120, the rear ring body 130 and the support body 140 are made of a low density material. In an embodiment, the low density material can be a material which can be imaged in X-ray imaging in relation to others, and the material provides nearly one time of contrast.

Preferably, the front ring body 110 has a hollow structure, so that an analyte is put in the loading table 120 along the virtual axis 200 from the side.

Figure 2:
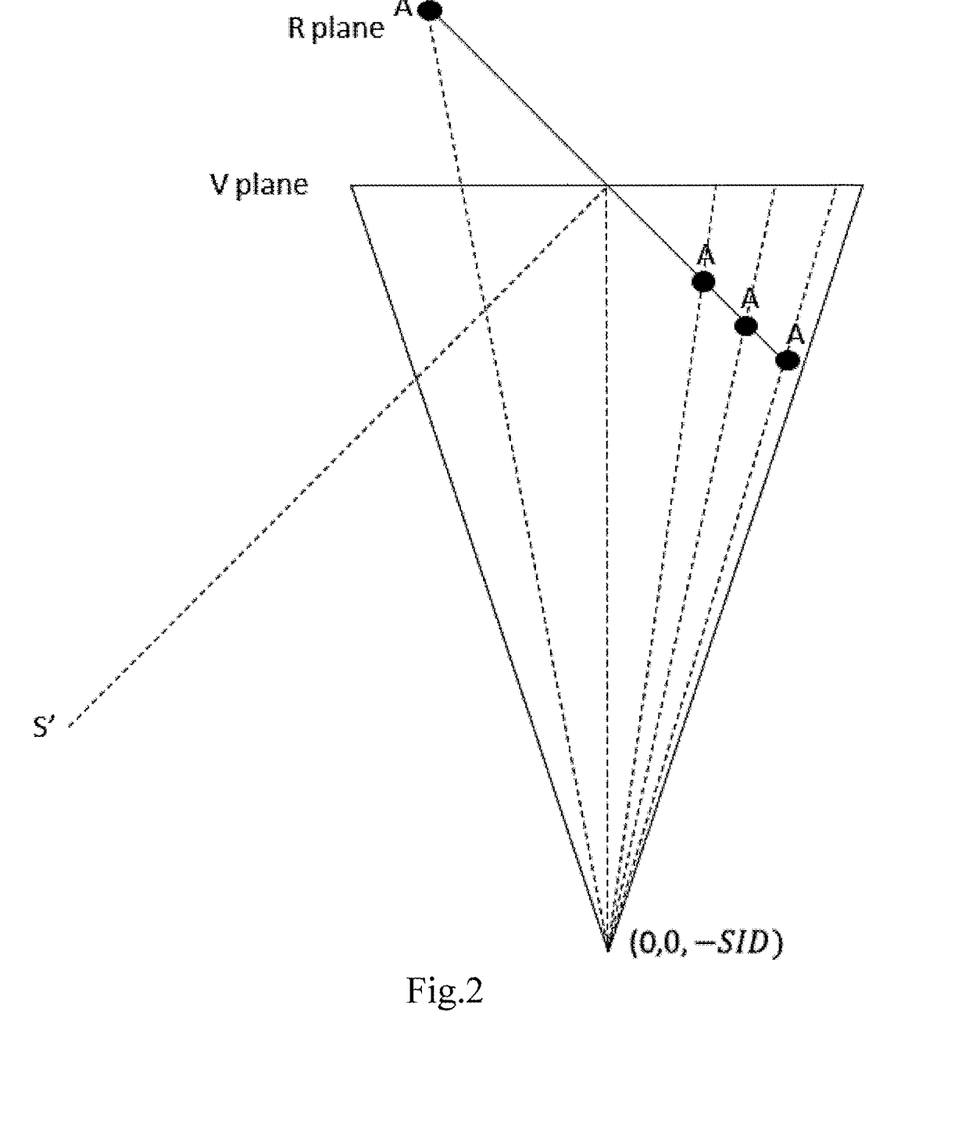
FIG. 2 is the graph of relation between the phantom and projection plane of the present invention.

The present invention uses reprojection to reproject the 2D projection image collected by the actual detector on the ideal detector plane. The purpose is to obtain the 2D projection image collected by ideal detector through geometric parameters, as shown in FIG. 2, wherein V plane is the ideal detector plane, R plane is the actual detector plane, s' is the actual light source position, the ideal light source position is (0, 0, −SID), A is the projection point of a plurality of positioning beads.

Figure 3:
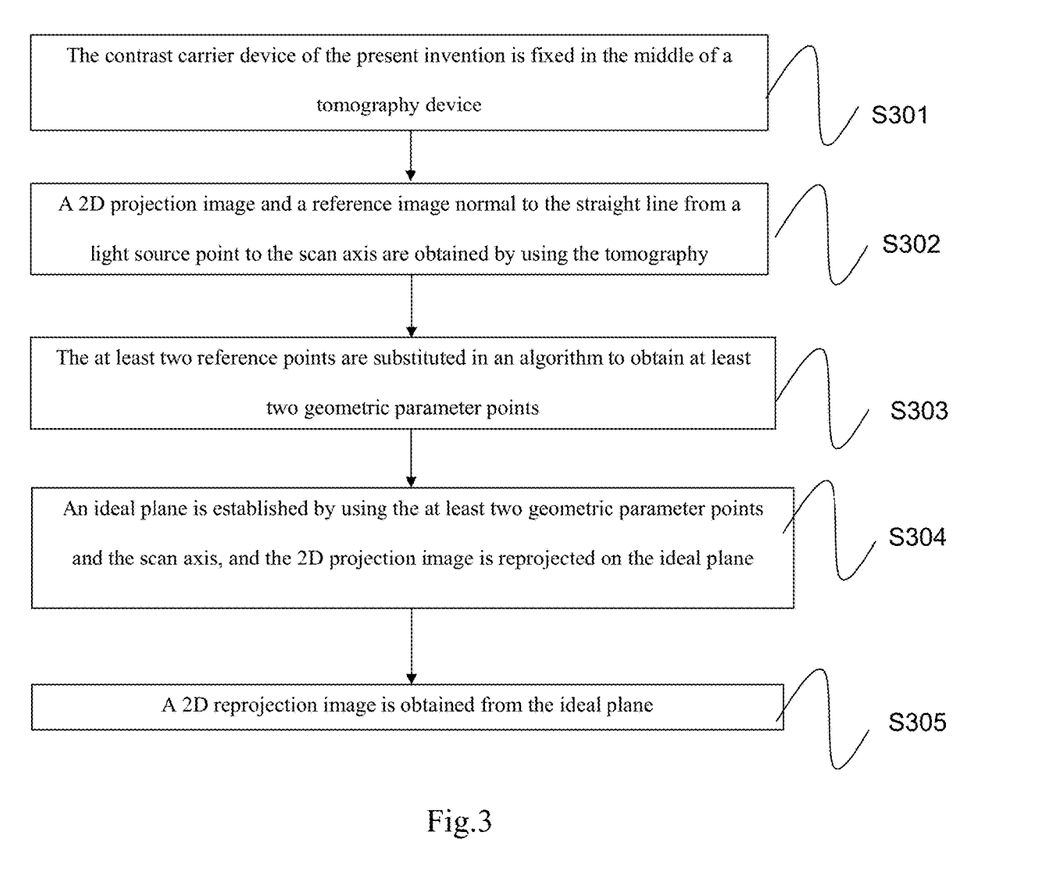
FIG. 3 is the flow diagram of the correction method of the present invention.

The present invention provides a correction method for tomography instruments, as shown in FIG. 3, the steps include (a) the contrast carrier device 100 of the present invention is fixed in the middle of a tomography device, and the contrast carrier device 100 has a virtual axis 200 which coincides with a scan axis of the tomography device S301; (b) a 2D projection (Object images) image and a reference image normal to the straight line from a light source point to the scan axis are obtained by using the tomography instrument based on the scan axis, wherein the reference image has at least two reference points (Dual ring images) S302; (c) the at least two reference points are substituted in an algorithm, at least two geometric parameter points are obtained S303; (d) an ideal plane is established by using the at least two geometric parameter points and the scan axis, the 2D projection image (Object images) is reprojected on the ideal plane S304; and (e) a 2D reconstruction image is obtained from the ideal plane S305.

Preferably, the two reference points in Step (b) contain the projection of front correction bead 112 and rear correction bead 121 or the projection of front positioning bead 113 and rear positioning bead 133.

Furthermore, Step (d) contains (d1) wherein the ideal plane contains a plurality of ideal coordinate points, a plurality of linear equations is obtained from the straight lines from the ideal coordinate points to the light source point; (d2) a simultaneous equation is derived from the algorithm and the linear equations; (d3) wherein the 2D projection image contains a plurality of image coordinate points with a pixel respectively, the image coordinate points project the pixels on the corresponding ideal coordinate points through the simultaneous equation.

Preferably, the algorithm is a motion equation or a rotation equation.

Figure 4:
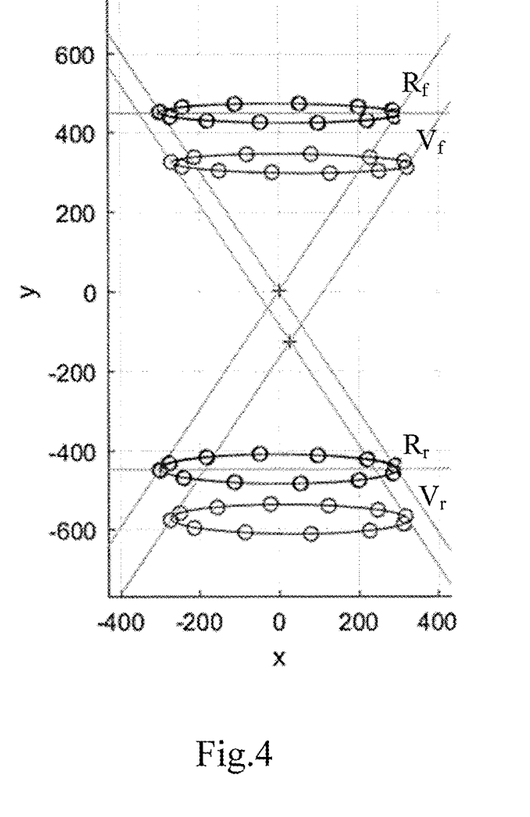
FIG. 4 is the graph of the relation between calculated position beads from realistic projection and the ideal projection.

Preferably, the at least two reference points comprise the points of at least two parallel circular rings. In an embodiment, as shown in FIG. 4, there are five positioning bead point positions on the front outer peripheral surface $R_f$, $V_f$ and rear outer peripheral surface $R_r$, $V_r$ respectively, the positioning beads are elliptically distributed in the image. As the elliptic equation has five unknown numbers (a, b, c, $u_0$, $v_0$), expressed as follows, the rotation and translation are performed according to reprojection, the 10 steel ball point positions after movement can be obtained, substituted in geometric parameter correction procedures for calculation, the 2D reprojection image is obtained.

$$a(u-u_0)^2+b(v-v_0)^2+2c(u-u_0)(v-v_0)=1$$

In order to make sure the geometric correction and actual image contrast can be performed synchronously, the present invention uses two standard phantoms to quantitatively analyze the 3D-FDK and OSEM image quality before and after correction. The two standard phantoms are Micro-CT water phantom developed by QRM GmbH, which is a cylinder, filled with distilled water for image quality analysis, so as to judge the image noise and uniformity; and Micro-CT contrast scale phantom, which is a cylinder, the cylindrical center has two materials, which are iodine and HA (calcium hydroxyapatite) for contrast analysis.

Figure 5A:
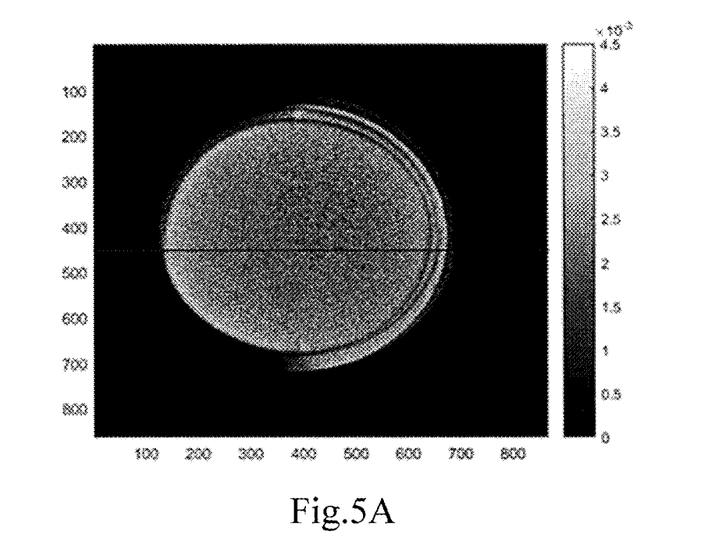
FIG. 5A to FIG. 5D show the result of water phantom reconstructed by using 3D-FDK algorithm.
Figure 5B:
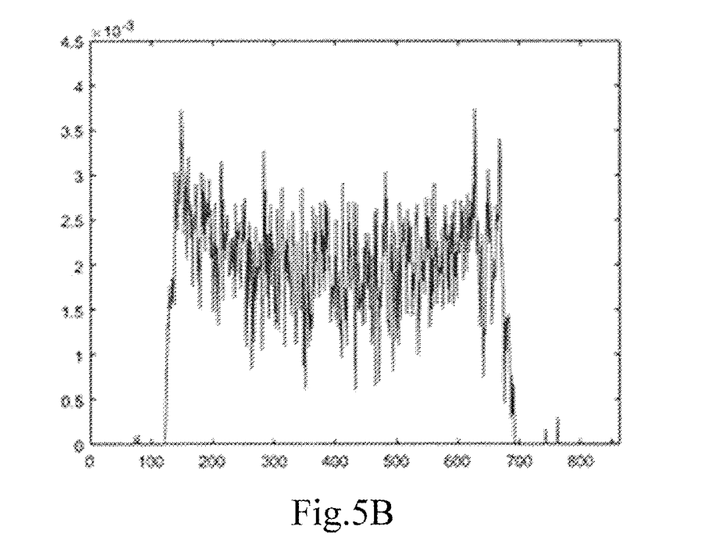
Figure 5C:
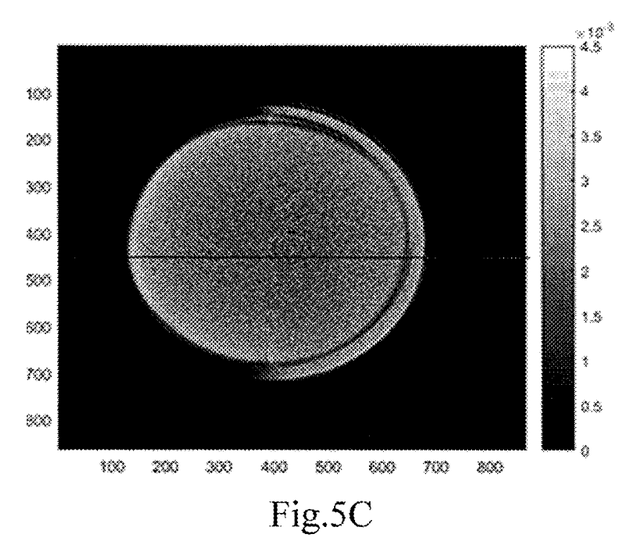
Figure 5D:
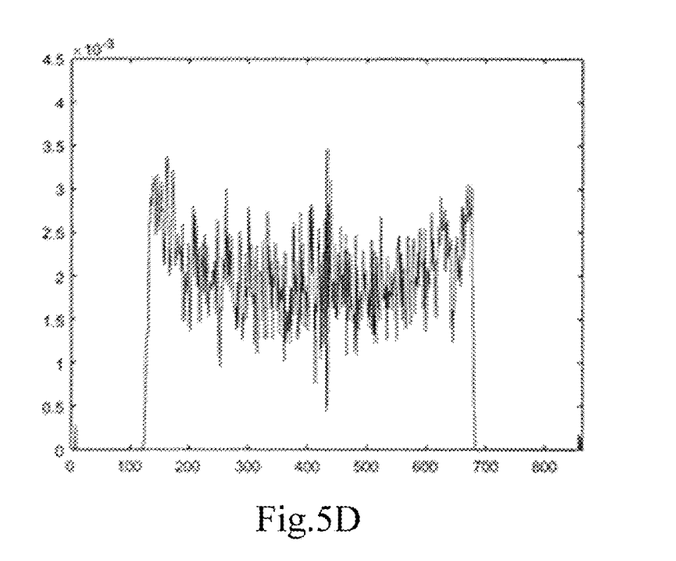

1. Contrast Scale Phantom:

FIG. 5A to FIG. 5D show the result of water phantom reconstructed by 3D-FDK, wherein FIG. 5A and FIG. 5B show the image before correction, FIG. 5C and FIG. 5D show the image corrected by the present invention. The x-directions when y=432 (½ detector size) are compared, it is found that the blurred geometric phantom at the phantom edge can be improved after correction, especially at the semi-circular arc edge, the complete profile image can be observed in the corrected image.

Figure 6A:
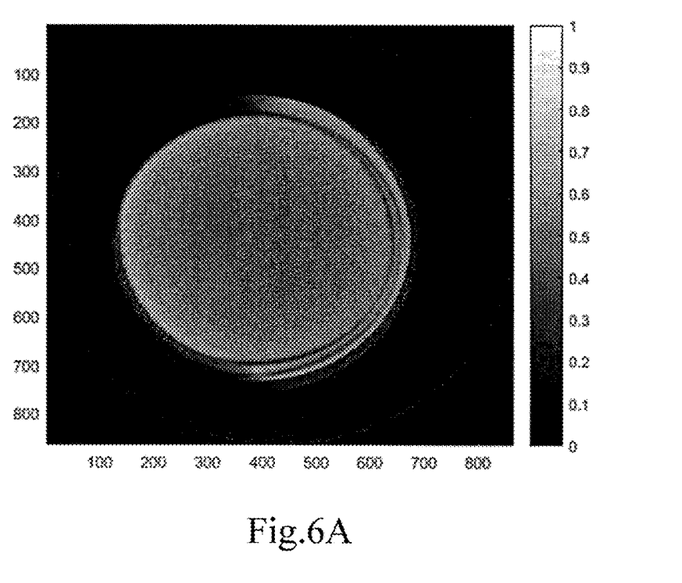
FIG. 6A to FIG. 6D show the result of water phantom reconstructed by using OSEM algorithm.
Figure 6B:
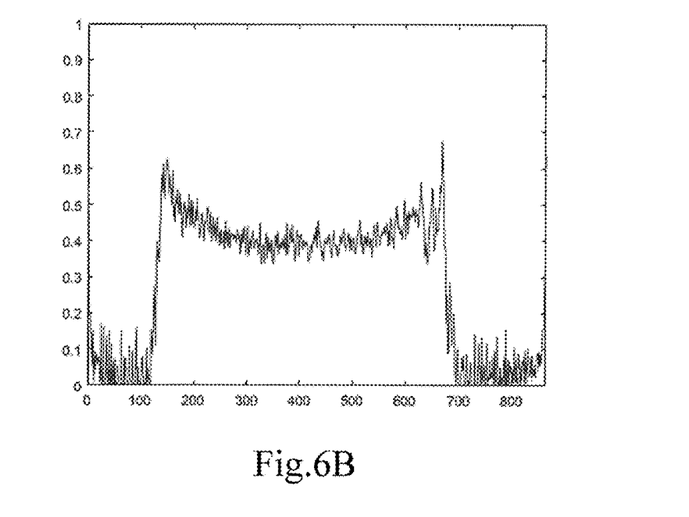
Figure 6C:
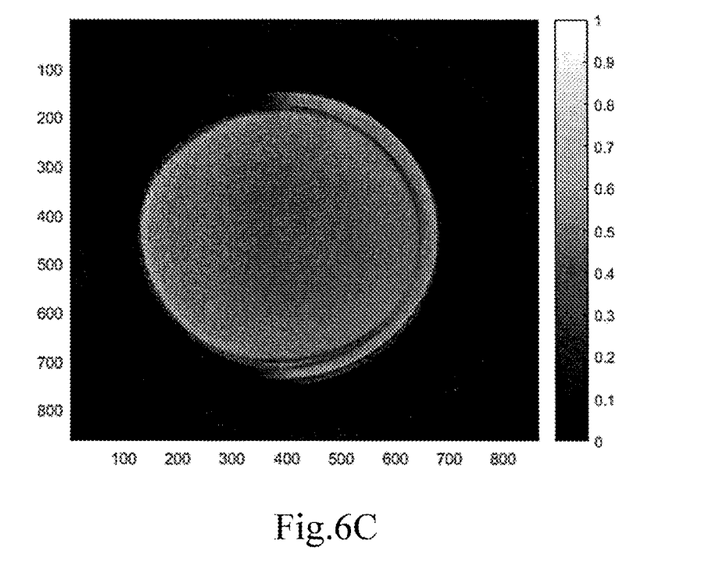
Figure 6D:
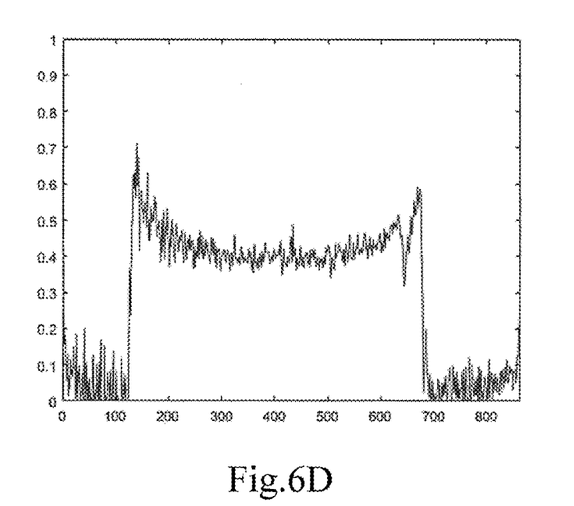

FIG. 6A to FIG. 6D show the reconstruction result of Water phantom iterated by OSEM, wherein FIG. 6A and FIG. 6B are the image before correction, FIG. 6C and FIG. 6D are the image corrected by the present invention. In comparison to 3D-FDK reconstruction, there is less image noise after OSEM reconstruction. According to the image edges before and after correction, the gap between the fixed part and phantom is more apparent in the corrected image.

Figure 7A:
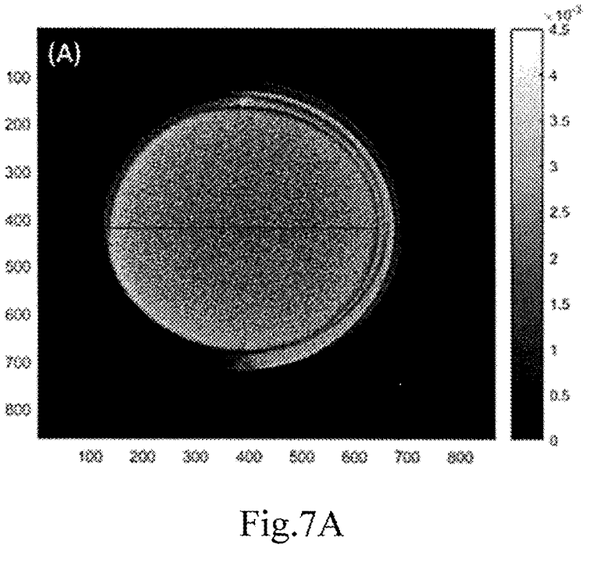
FIG. 7A and FIG. 7B show the analysis of geometric deformation of water phantom.
Figure 7B:
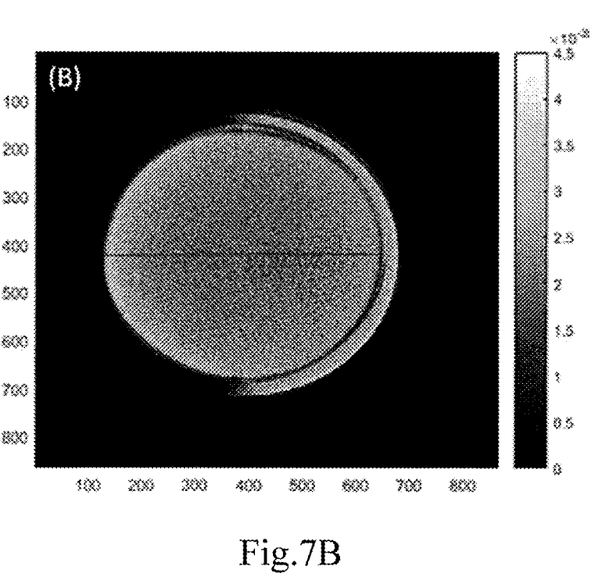

FIG. 7A and FIG. 7B disclose the geometric deformation of water phantom, the distance of the measured diameter is multiplied by voxel size and converted into length (mm), the phantom diameters of the image before correction, image after correction and true value are compared, the result is shown in Table 1.

TABLE 1

Measured value of water phantom diameter

| Measured value (mm) true value = 32 | Before correction | After correction |
| --- | --- | --- |
| 3D-FDKreconstruction | 33.02 | 32.96 |
| OSEM reconstruction | 33.02 | 32.96 |

According to the specifications of water phantom, the diameter of phantom is 32 mm, the calculation error amounts are shown in Table 2. The error is reduced by 0.75% after correction of 3D-FDK reconstruction or OSEM reconstruction.

TABLE 2

Error of water phantom diameter

| Error (%) | Before correction | After correction |
| --- | --- | --- |
| 3D-FDKreconstruction | 3.75% | 3.00% |
| OSEM reconstruction | 3.75% | 3.00% |

2. Contrast Scale Phantom

Figure 8A:
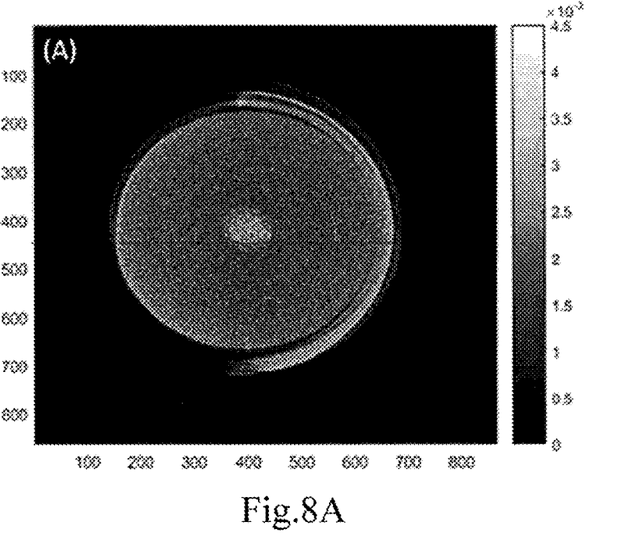
FIG. 8A to FIG. 8D show the result of contrast scale phantom reconstructed by using 3D-FDK algorithm.
Figure 8B:
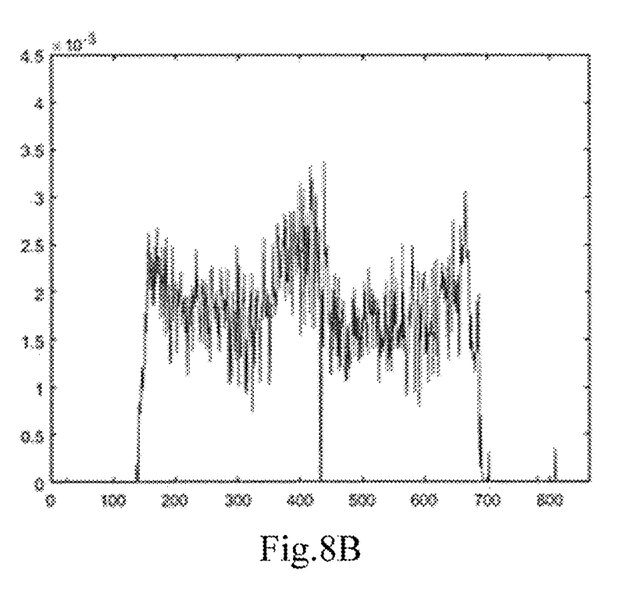
Figure 8C:
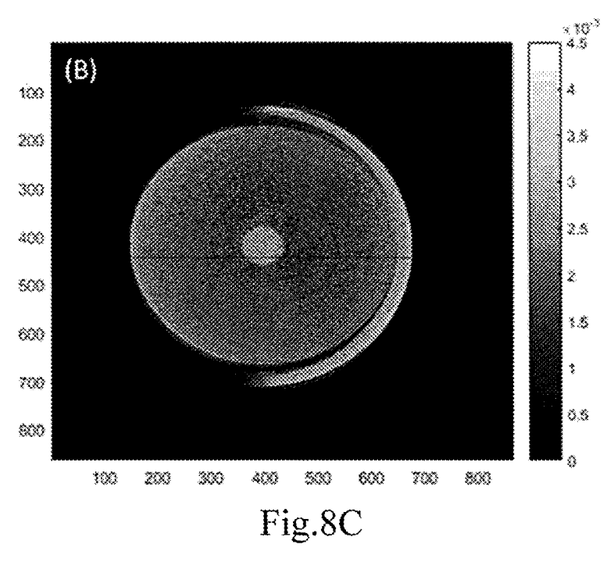
Figure 8D:
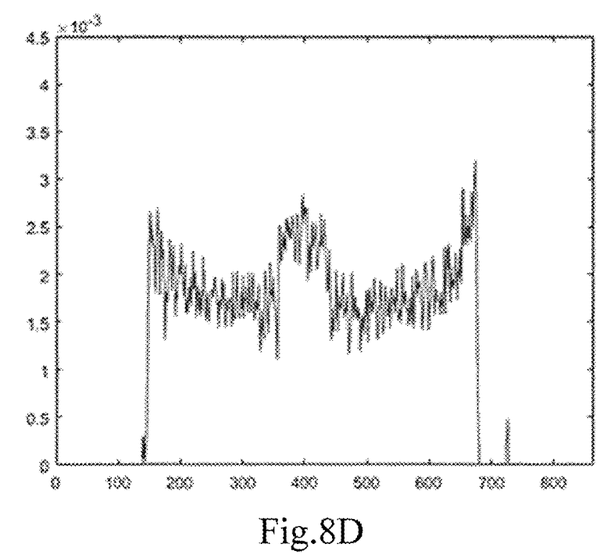

FIG. 8A to FIG. 8D show the result of contrast scale phantom reconstructed by 3D-FDK. FIG. 8A and FIG. 8B are the image before correction, FIG. 8C and FIG. 8D are the image corrected by the present invention, the x-directions when y=432 (½ detector size) are compared, it is observed that there are obvious differences in the middle material, and the geometric phantom is observed on the outer ring of the image before correction, the geometric phantom of the image after correction is improved.

Figure 9A:
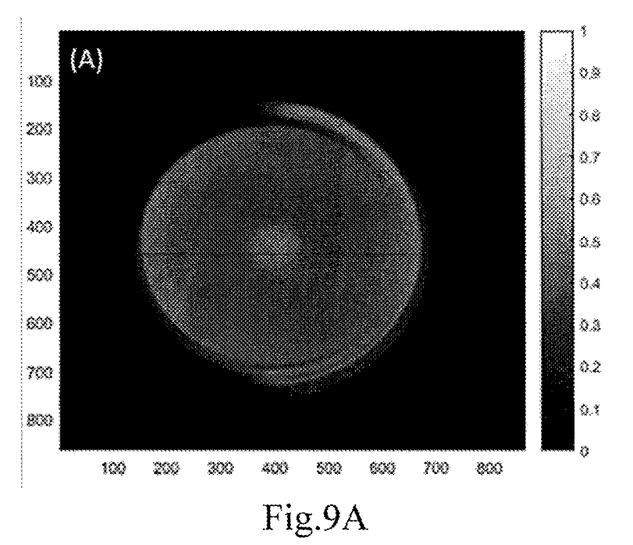
FIG. 9A to FIG. 9D show the result of contrast scale phantom reconstructed by using OSEM algorithm.
Figure 9B:
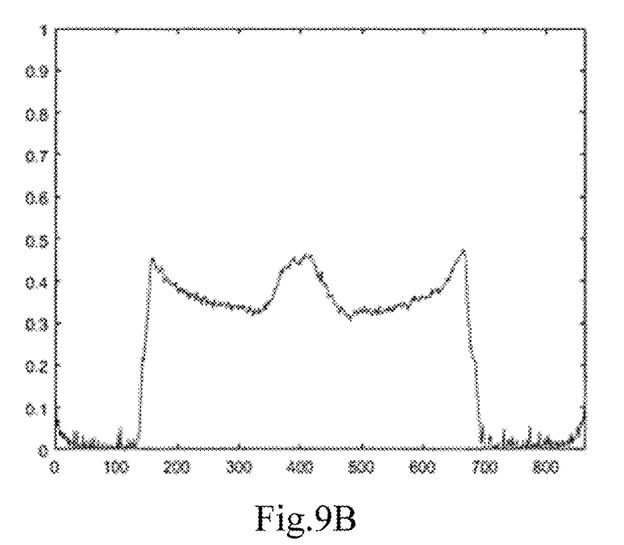
Figure 9C:
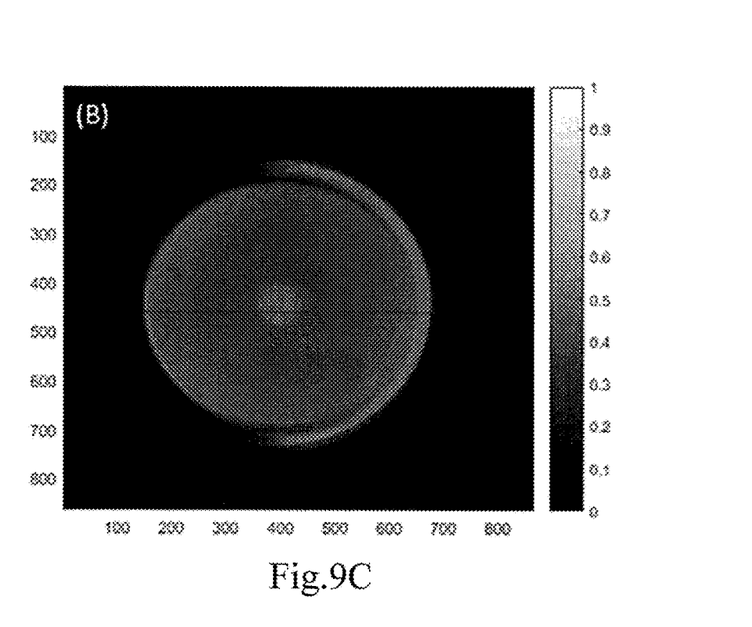
Figure 9D:
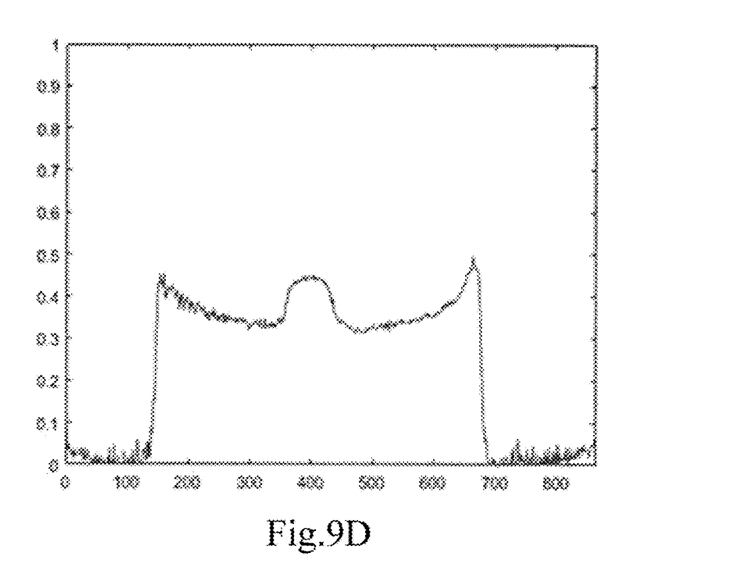

FIG. 9A to FIG. 9D show the reconstruction result of contrast scale phantom iterated by OSEM, FIG. 9A and FIG. 9B show the result before correction, FIG. 9C and FIG. 9D show the correction result of the present invention. In comparison to 3D-FDK reconstruction, the image reconstructed by OSEM has less noise, and there are differences in the central column.

Figure 10A:
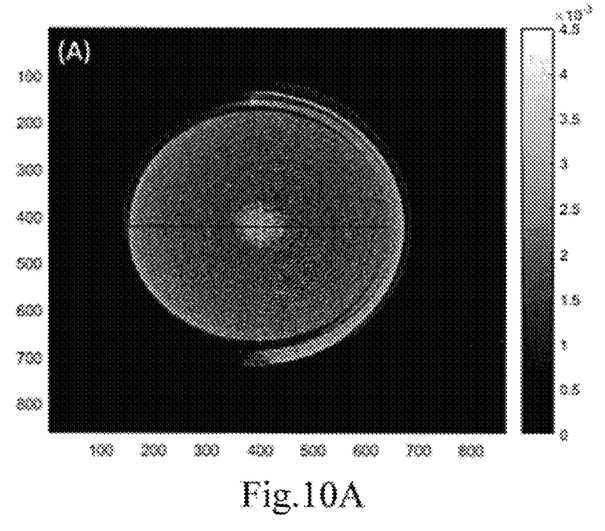
FIG. 10A and FIG. 10B show the analysis of geometric deformation of contrast scale phantom.
Figure 10B:
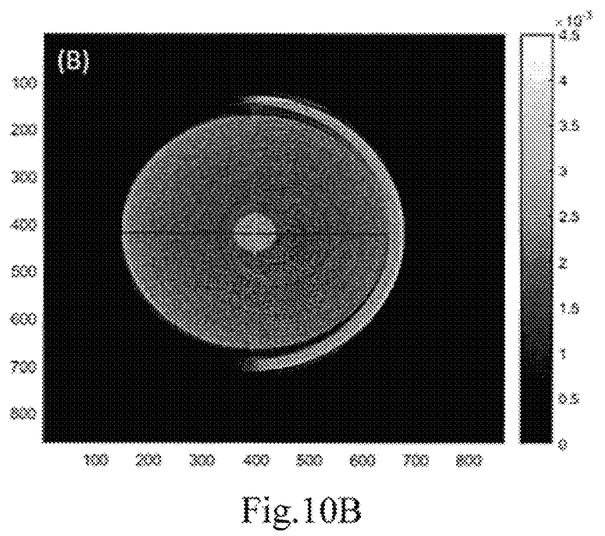

FIG. 10A and FIG. 10B disclose the geometric deformation of Contrast scale phantom, the diameter of phantom and the diameter of cylindrical material in the phantom center are measured respectively and multiplied by voxel size, converted into length (mm), the phantom diameters of image before correction, image after correction and true value are compared. The results are shown in Table 3 and Table 4.

TABLE 3

Measured diameter of contrast scale phantom

| Measured value (mm) true value = 32 | Before correction | After correction |
| --- | --- | --- |
| 3D-FDKreconstruction | 37.5 | 37.2 |
| OSEM reconstruction | 37.57 | 37.57 |

TABLE 4

Measured diameter of central cylinder of contrast scale phantom

| Measured value (mm) true value = 5 | Before correction | After correction |
| --- | --- | --- |
| 3D-FDKreconstruction | 7.07 | 6.03 |
| OSEM reconstruction | 6.92 | 5.95 |

According to the specifications of contrast scale phantom, the diameters are 32 mm and 5 mm, the calculation errors are shown in Table 5 and Table 6. The diameter error is not improved obviously, but there is obvious effect on the central cylinder. The errors of the two reconstruction methods are reduced by about 20% after correction.

TABLE 5

Errors of contrast scale phantom diameter

| Error (%) | Before correction | After correction |
| --- | --- | --- |
| 3D-FDKreconstruction | 17.19% | 16.25% |
| OSEM reconstruction | 17.41% | 17.41% |

TABLE 6

Diameter errors of central cylinder of contrast scale phantom

| Error (%) | Before correction | After correction |
|---|---|---|
| 3D-FDKreconstruction | 41.40% | 20.60% |
| OSEM reconstruction | 38.40% | 19.00% |

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

The invention claimed is:

1. A contrast carrier device with geometric calibration phantom on computed tomography, comprising:
    a front ring body with a front outer peripheral surface, the front outer peripheral surface is provided with a front correction bead;
    a loading table, wherein one end of the loading table is connected with the front ring body;
    a rear ring body, the rear ring body is oppositely arranged at the other end of the front ring body connected to the loading table, wherein the rear ring body has a rear outer peripheral surface, the rear outer peripheral surface is provided with a rear correction bead;
    a virtual axis passes through the center of the front ring body and the center of the rear ring body respectively, the front correction bead and the rear correction bead are arranged equidistantly along the virtual axis; and
    a support body, the support body is provided opposite to the other end of the rear ring body connected to the loading table, so that the contrast carrier device is fixed to a tomography device, and the virtual axis coincides with a scan axis of the tomography device.

2. The contrast carrier device defined in claim 1, wherein the front outer peripheral surface is provided with a plurality of front positioning beads, wherein the plurality of front positioning beads and the front correction bead are equiangularly arranged on the front outer peripheral surface along the virtual axis.

3. The contrast carrier device defined in claim 2, wherein the rear outer peripheral surface is provided with a plurality of rear positioning beads, the plurality of rear positioning beads and the rear correction bead are equiangularly arranged on the rear outer peripheral surface along the virtual axis, and the plurality of front positioning beads and the plurality of rear positioning beads are arranged equidistantly along the virtual axis pairwise.

4. The contrast carrier device defined in claim 3, wherein the front correction bead, the rear correction bead, the plurality of front positioning beads and the plurality of rear positioning beads are made of a high density material.

5. The contrast carrier device defined in claim 4, wherein the high density material is metal material or a material which can be imaged in X-ray image in relation to others, and the material provides over 10 times of contrast.

6. The contrast carrier device defined in claim 5, wherein the diameter ratio range of the front correction bead, the rear correction bead, the plurality of front positioning beads and the plurality of rear positioning beads is 1:1:0.1~0.4:0.1~0.4.

7. The contrast carrier device defined in claim 1, wherein the front ring body, the loading table, the rear ring body and the support body are made of a low density material.

8. The contrast carrier device defined in claim 7, wherein the low density material is a material which can be imaged in X-ray image in relation to others, and the material provides at most one-time of contrast.

9. The contrast carrier device defined in claim 6, wherein the front ring body has a hollow structure, so that an object is put in the loading table along the virtual axis from the side.

10. A tomography instrument correction method, the steps include:
    (a) a contrast carrier device stated in claim 1 is fixed in the middle of a tomography device, and the contrast carrier device has a virtual axis which coincides with a scan axis of the tomography device;
    (b) a 2D projection image and a reference image normal to the straight line from a light source point to the scan axis are obtained by using the tomography instrument based on the scan axis, wherein the reference image has at least two reference points;
    (c) the at least two reference points are substituted in an algorithm to obtain at least two geometric parameter points;
    (d) an ideal plane is established by using the at least two geometric parameter points and the scan axis, and the 2D projection image is reprojected on the ideal plane; and
    (e) a 2D reprojection image is obtained from the ideal plane.

11. The method defined in claim 10, the two reference points in Step (b) contain the projection of front correction bead and rear correction bead or the projection of front positioning bead and rear positioning bead.

12. The method defined in claim 10, Step (d) contains:
    (d1) the ideal plane contains a plurality of ideal coordinate points, a plurality of linear equations is obtained from the straight lines between the ideal coordinate points and the light source point;
    (d2) a simultaneous equation is obtained from the algorithm and the linear equations; and
    (d3) the 2D projection image contains a plurality of image coordinate points with a pixel respectively, the image coordinate points project the pixels on the corresponding ideal coordinate points through the simultaneous equation.

13. The method defined in claim 12, the algorithm is a motion equation or a rotation equation.

14. The method defined in claim 10, the at least two reference points comprise the points of at least two parallel circular rings.

* * * * *